(12) United States Patent
Ohta et al.

(10) Patent No.: US 8,647,305 B2
(45) Date of Patent: Feb. 11, 2014

(54) SYRINGE DRIVE DEVICE

(75) Inventors: Akihiro Ohta, Osaka (JP); Tohru Nakamura, Osaka (JP); Osamu Mizuno, Osaka (JP); Soichiro Fujioka, Osaka (JP); Akinobu Okuda, Nara (JP); Tsuyoshi Tojo, Osaka (JP)

(73) Assignee: Panasonic Corporation, Osaka (JP)

( * ) Notice: Subject to any disclaimer, the term of this patent is extended or adjusted under 35 U.S.C. 154(b) by 123 days.

(21) Appl. No.: 13/257,338

(22) PCT Filed: Mar. 23, 2010

(86) PCT No.: PCT/JP2010/002030
§ 371 (c)(1),
(2), (4) Date: Sep. 19, 2011

(87) PCT Pub. No.: WO2010/119622
PCT Pub. Date: Oct. 21, 2010

(65) Prior Publication Data
US 2012/0016303 A1    Jan. 19, 2012

(30) Foreign Application Priority Data
Apr. 14, 2009    (JP) .................................. 2009-097838

(51) Int. Cl.
*A61M 5/00*    (2006.01)
(52) U.S. Cl.
USPC .......................................................... 604/181
(58) Field of Classification Search
USPC .................................. 604/272, 131, 181–243
See application file for complete search history.

(56) References Cited

U.S. PATENT DOCUMENTS

| 3,640,431 | A | * | 2/1972 | Plumer .......................... 222/48 |
| 5,269,762 | A | | 12/1993 | Armbruster et al. |
| 2001/0012926 | A1 | * | 8/2001 | Gross et al. ................... 604/272 |
| 2002/0183733 | A1 | * | 12/2002 | Mulier et al. ................... 606/28 |
| 2005/0234337 | A1 | | 10/2005 | Browne |

FOREIGN PATENT DOCUMENTS

| EP | 1 145 703 | 10/2001 |
| JP | 6-007440 | 1/1994 |
| JP | 2005-534446 | 11/2005 |
| WO | 00/38615 | 7/2000 |
| WO | 2007/026684 | 3/2007 |

OTHER PUBLICATIONS

International Search Report issued Jun. 22, 2010 in International (PCT) Application No. PCT/JP2010/002030.

* cited by examiner

*Primary Examiner* — Nicholas Lucchesi
*Assistant Examiner* — Pritesh Patel
(74) *Attorney, Agent, or Firm* — Wenderoth, Lind & Ponack, L.L.P.

(57) ABSTRACT

A syringe drive device drives a syringe including a cylindrical cylinder and a piston. The cylinder includes a solution supply port at one end, and an opening at the other end. The piston is inserted into the cylinder through the opening. The syringe drive device includes a cylinder holder to rotatably hold the cylinder of the syringe, and a piston driver to drive the piston in its axial direction with respect to the cylinder held in the cylinder holder.

8 Claims, 9 Drawing Sheets

SYRINGE DRIVE DEVICE

TECHNICAL FIELD

The invention relates to a syringe drive device for driving a syringe by moving the piston in and out of the syringe.

RELATED ART

As well known, in hospitals, an IV (intravenous drip) medicine is prepared by drawing a plurality of bottled medicines into a syringe and mixing them in the syringe. The prepared medicine is then pushed out of the syringe into, for example, an IV bag.

The syringe includes a cylinder and a piston. The cylinder has a solution supply port at one end, and an opening at the other end. The piston is inserted into the cylinder from the opening at the other end. The piston is pulled out of the cylinder to draw a medicine out of a medicine bottle, and is pushed into the cylinder to inject the medicine into an IV bag.

To draw a medicine out of a medicine bottle, the user has to continue to pull the piston against the negative pressure generated when the user pulls the piston. To inject the medicine into an IV bag, on the other hand, the user has to continue to push the piston against the positive pressure generated by a filter disposed in the injection path. The reaction force due to the negative or positive pressure is as large as several tens of newtons.

When preparing a medicine, the user generally holds a medical bottle or an IV bag in one hand, and a syringe in the other hand. In some cases, the syringe and the medical bottle or the IV bag have to be held in proper positional relationship. This forces the user to push and pull the piston into/out of the syringe alternately against several tens of newtons while properly holding the syringe in the proper position with the opposite hand.

To solve this problem, there has been proposed a device for supporting the user to use a syringe to administer a predetermined amount of medicine to a person.

FIG. 11A is a perspective view of conventional syringe drive device 110, and FIG. 11B is an enlarged view of an essential part of syringe drive device 110.

As shown in FIG. 11A, syringe drive device 110 includes piston driver 116, and cylinder holder 120 which holds cylinder 151 of syringe 150 at flange 152 of cylinder 151 (see, for example, WO07/026,684). Piston driver 116 moves piston 155 backward or forward in the axial direction of piston 155 with respect to cylinder 151 held in cylinder holder 120, thereby forcing a medicine into/out of cylinder 151. Syringe 150 is placed in recess 114 and cylinder holder 120 of syringe drive device 110 such that flange 152 of syringe 150 is fitted into holding slit 123. Cylinder holder 120 includes fixed holder 121 and left and right movable holders 122. Movable holders 122 can be fixed or released to attach or detach syringe 150 to/from syringe drive device 110.

As shown in FIG. 11B, cylinder 151 is rotated in the direction of the arrow such that projections 155a of cylinder holder 120 are fitted into recesses 153 formed in flange 152. This is how the syringe drive device of WO07/026,684 prevents unintended rotation of cylinder 151.

In this conventional syringe drive device, however, the cylinder holder fixes the cylinder both in the axial and circumferential directions. This forces the user to release the cylinder from the cylinder holder whenever the cylinder needs to be rotated, for example, for air purging.

The detailed description is as follows. The solution supply port at the tip of the cylinder is in a position eccentric to the central axis (for example, at the bottom of the periphery). Therefore, if air has entered the cylinder together with a medicine, the user has to purge the air before drawing the next medicine into the cylinder or injecting the medicine into an IV bag.

As described above, the solution supply port at the tip of the cylinder is in a position eccentric to the central axis (for example, at the bottom of the periphery). Therefore, during air purging, the user rotates the cylinder until the solution supply port is positioned at the top of the periphery of the cylinder, thereby preventing the flow of the medicine from the cylinder.

In this conventional syringe drive device, however, a complex process is required to rotate the cylinder as follows. The user first has to release the cylinder from the cylinder holder for air purging or other purposes, then rotate the cylinder, and fix the cylinder on the cylinder holder again.

SUMMARY OF THE INVENTION

In view of the above-described problems, it is an object of the invention to provide a user-friendly syringe drive device which facilitates performing air purging.

The syringe drive device of the invention holds and drives a syringe which includes a cylinder and a piston inserted therein. The syringe drive device includes a cylinder holder and a piston driver. The cylinder holder holds the cylinder such that the cylinder can rotate around a plane perpendicular to the shaft of the cylinder. The piston driver drives the piston in the axial direction thereof with respect to the cylinder held in the cylinder holder.

With this structure, to purge air or for other purposes, the user can rotate the cylinder while holding it in one hand. Thus, the syringe drive device is extremely user-friendly.

DESCRIPTION OF EMBODIMENTS

Figure 1:
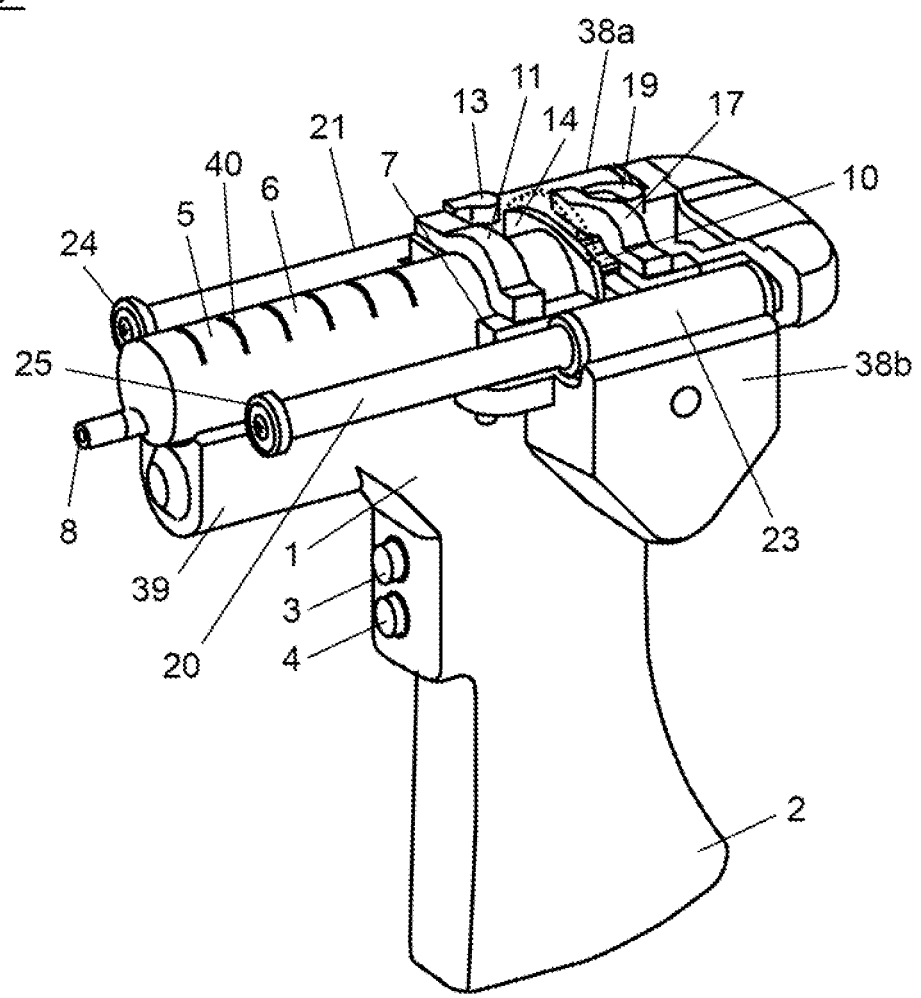
FIG. 1 is a perspective view of a syringe drive device according to a first embodiment of the invention.

Embodiments of the invention will be described as follows with reference to the accompanied drawings. In these drawings, the same components are denoted by the same reference numerals, and the description thereof may be omitted.

First Embodiment

Figure 2:
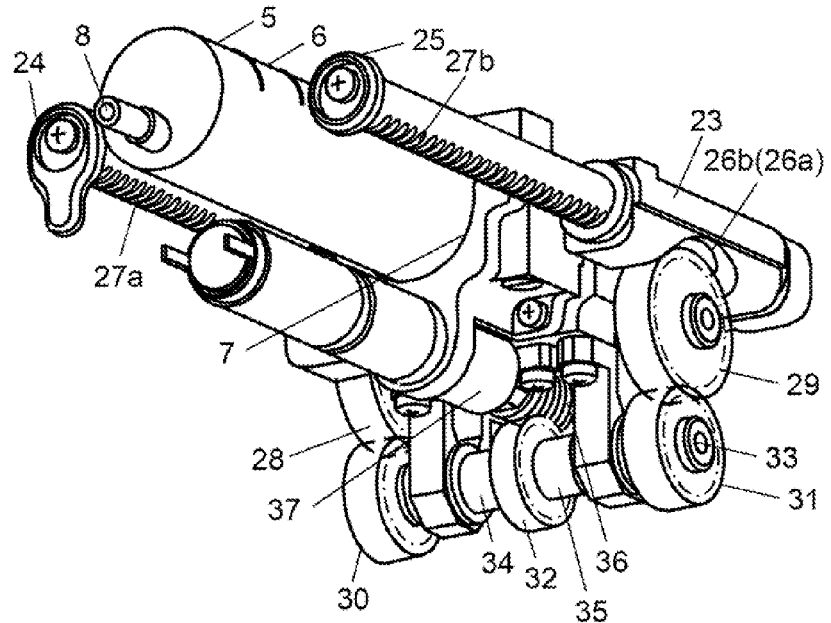
FIG. 2 is a perspective view of a first example of mechanism elements of the syringe drive device according to the first embodiment of the invention.
Figure 3:
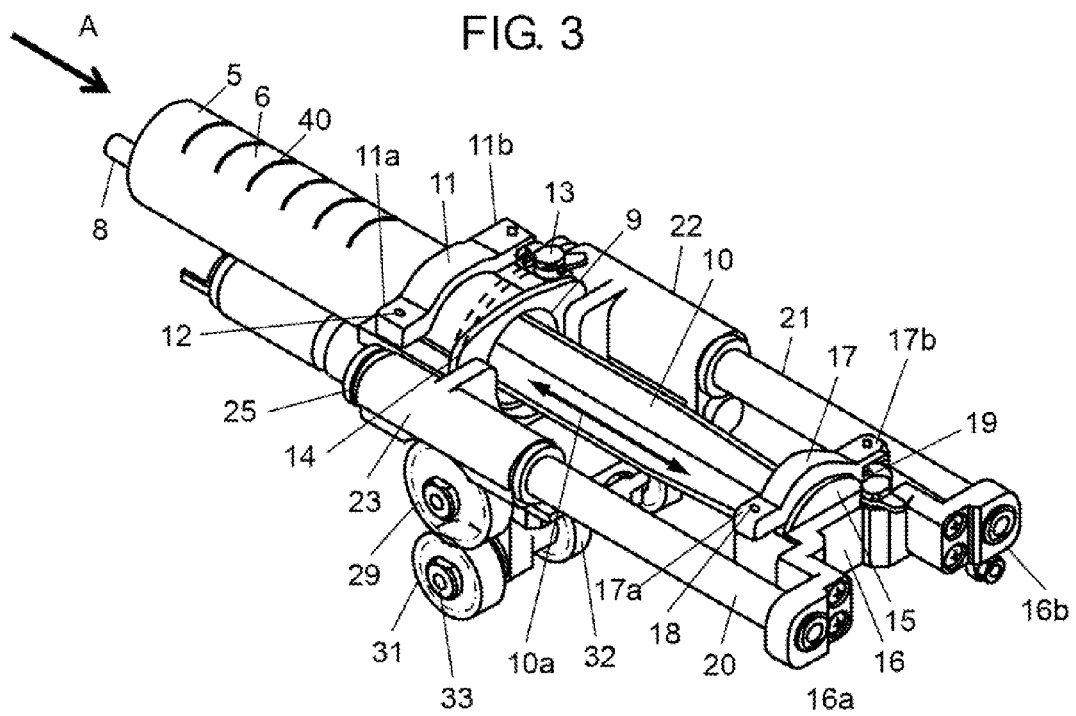
FIG. 3 is a perspective view of a second example of the mechanism elements of the syringe drive device according to the first embodiment of the invention.
Figure 4:
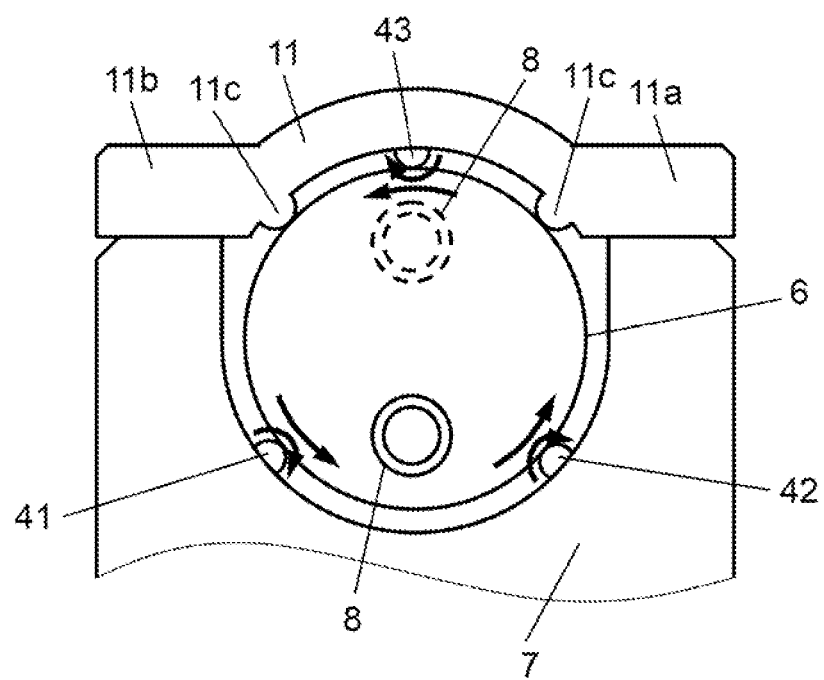
FIG. 4 shows the syringe drive device viewed from the direction of "A" in FIG. 3.

FIG. 1 is a perspective view of a syringe drive device according to a first embodiment of the invention. FIGS. 2 and 3 are perspective views of first and second examples, respectively, of mechanism elements of the syringe drive device. FIG. 4 shows the syringe drive device viewed from the direction of "A" in FIG. 3.

FIGS. 2 and 3 show the mechanism elements of syringe drive device 100 where body case 1 and covers 38b, 39 are not illustrated. The description of these drawings is based on the condition that body case 1 and covers 38b, 39 are eliminated.

In FIG. 1, syringe drive device 100 includes body case 1 and grip 2 at the bottom of body case 1.

Syringe drive device 100 of the first embodiment is designed to be portable as described above. The user can hold grip 2 in the right hand like holding a pistol, and operate operation buttons 3 and 4 with the index finger placed behind grip 2 in FIG. 1.

As shown in FIG. 2, syringe drive device 100 further includes, over body case 1, cylinder holder 7 which holds cylinder 6 of syringe 5.

As understood from FIG. 3, syringe 5 includes cylindrical cylinder 6 and piston 10. Cylinder 6 has solution supply port 8 at one end, and opening 9 at the other end. Piston 10 is inserted into cylinder 6 from opening 9 at the other end.

As understood from FIG. 4, cylinder holder 7 has a semicircular recess in its top surface. Cylinder holder 7 includes hold-down bar 11, which is placed on the top surface of cylinder 6 while the back of cylinder 6 with opening 9 is being held as shown in FIGS. 1 to 4.

Hold-down bar 11 includes shaft 12 at one end 11a while other end 11b is free. Hold-down bar 11 further includes a spring (not shown) under shaft 12. The user can raise one end 11a of hold-down bar 11 against the tensile strength of the spring, and rotate the other (free) end 11b in the counterclockwise direction by 90 degrees while one end 11a is in the raised position.

To set cylinder 6 in cylinder holder 7, the user first raises one end 11a of hold-down bar 11 against the tensile strength of the spring, and then rotates other end 11b in the counterclockwise direction by 90 degrees to open the top surface of cylinder holder 7.

In this situation, the user rotates other end 11b of hold-down bar 11 in the clockwise direction by 90 degrees. As shown in FIGS. 1 and 3, hold-down bar 11 covers the top of cylinder 6 to complete the setting of cylinder 6.

Cylinder holder 7 includes lock claw 13 at other end 11b of hold-down bar 11 as shown in FIG. 3. After the setting of cylinder 6 is completed, lock claw 13 is engaged with hold-down bar 11 in order to prevent hold-down bar 11 from becoming detached from cylinder 6.

Cylinder 6 includes non-slip flange 14 at its rear end, and cylinder holder 7 has a groove (not shown) into which flange 14 is fitted. As shown in FIGS. 1 and 3, when cylinder 6 is set in cylinder holder 7, the groove defines the position of flange 14. This allows cylinder 6 to be held horizontally in the central axis direction. The groove into which flange 14 is fitted is in the shape of a semicircular recess around which that flange 14 can rotate.

As shown in FIG. 3, piston 10 includes flange 15 at its rear end (outside cylinder 6 when piston 10 is inserted in cylinder 6). Syringe drive device 100 further includes piston-operating rod 16 and piston restraint 17. Flange 15 comes into contact with piston-operating rod 16. Piston restraint 17 is disposed on the other side of piston-operating rod 16 with flange 15 therebetween such that flange 15 is restrained by piston-operating rod 16.

Similar to hold-down bar 11, piston restraint 17 includes shaft 18 at one end 17a while other end 17b is free. Piston restraint 17 further includes a spring (not shown) under shaft 18. The user can raise one end 17a against the tensile strength of the spring, and then rotate other end 17b in the clockwise or counterclockwise direction by 90 degrees while one end 17a is in the raised position.

To bring flange 15 at the rear end of piston 10 into contact with piston-operating rod 16, the user first raises one end 17a of piston restraint 17 against the tensile strength of the spring, and then rotates other end 17b in the clockwise direction by 90 degrees to open the top surface of piston 10 while one end 17a is in the raised position.

In this situation, the user rotates other end 17b of piston restraint 17 in the counterclockwise direction by 90 degrees. As shown in FIGS. 1 and 3, flange 15 is fixed between piston-operating rod 16 and piston restraint 17 to complete the setting of piston 10.

Cylinder holder 7 includes lock claw 19 at other end 17b of piston restraint 17 as shown in FIG. 3. After the setting of piston 10 is completed, lock claw 19 is engaged with piston restraint 17 in order to prevent flange 15 from becoming detached from piston-operating rod 16.

As shown in FIG. 3, piston-operating rod 16 is extended to both ends 16a and 16b orthogonal to axial direction 10a of piston 10, and is coupled to the rear end of columnar racks 20 and 21 at both ends 16a and 16b.

Syringe drive device 100 further includes shaft portions 22 and 23 on both sides of cylinder holder 7 so as to support the middle area of racks 20 and 21. As shown in FIG. 2, racks 20 and 21 have retainers 24 and 25 at their ends.

Shaft portions 22 and 23 have notches 26a and 26b, respectively, at their bottoms. Racks 20 and 21 have, at their bottoms, teeth 27 (27a, 27b) exposed at notches 26a and 26b.

Syringe drive device 100 further includes pinions 28 and 29 under notches 26a and 26b of shaft portions 22 and 23, respectively. Pinions 28 and 29 are respectively engaged with teeth 27a and 27b of racks 20 and 21 at notches 26a and 26b of shaft portions 22 and 23.

Syringe drive device 100 further includes pinions 30 and 31, which are disposed under pinions 28 and 29 respectively, and are engaged with pinions 28 and 29 respectively. Pinions 30 and 31 are rotated in unison with pinion 32 disposed therebetween.

Thus, pinions 30, 31, and 32 are on the same shaft 33, which is supported by left and right bearings 34 and 35 to rotate pinions 30, 31, and 32 in unison.

In this situation, pinion 32 is engaged with worm pinion 36, which is coupled to motor 37.

Motor 37 rotates clockwise when the user holds grip 2 shown in FIG. 1 in the right hand like holding a pistol and operates operation button 3 with the index finger placed behind grip 2 shown in FIG. 1. In this case, motor 37 drives worm pinion 36 and pinions 28, 29, 30, 31, and 32, thereby moving racks 20 and 21 rearward in axial direction 10a.

Piston-operating rod 16 is pulled rearward together with piston 10, allowing the medicine to be drawn from the medicine bottle into cylinder 6.

This operation will be described in detail. Although not shown in FIGS. 1 to 4, solution supply port 8 is provided with an injection needle (not shown). The user holds grip 2 with the right hand, and inserts the injection needle into the medicine bottle (not shown) held in the left hand in front of solution supply port 8.

When the user operates operation button 3 with the index finger of the right hand, motor 37 rotates clockwise. This rotates pinions 30 to 32 counterclockwise in FIG. 2, and pinions 28 and 29 clockwise. As a result, left and right racks 20 and 21 are moved rearward in axial direction 10a, thus being changed from the state shown in FIG. 2 to the state shown in FIG. 3.

As shown in FIG. 3, piston-operating rod 16 is coupled to the rear end of racks 20 and 21. Piston-operating rod 16 and piston restraint 17 together restrain flange 15 of piston 10. When left and right racks 20 and 21 are moved rearward in axial direction 10a, piston 10 is pulled out of cylinder 6. Thus, syringe drive device 100 can draw a medicine from the medicine bottle into cylinder 6.

To draw another medicine into cylinder 6, the user stops motor 37, and performs the same drawing operation to the next medicine bottle. As a result, a plurality of kinds of medicines are drawn and mixed in cylinder 6. This is the completion of the drawing and mixing of medicines.

When the user operates operation button 4 with the index finger of the right hand holding grip 2, motor 37 rotates counterclockwise. This rotates pinions 30 to 32 clockwise in FIG. 2, and pinions 28 and 29 counterclockwise. As a result left and right racks 20 and 21 are moved forward in axial direction 10a, thus being changed from the state shown in FIG. 3 to the state shown in FIG. 2.

When left and right racks 20 and 21 are moved forward in axial direction 10a in this manner, piston 10 is pushed into cylinder 6. As a result, the medicine in cylinder 6 is injected into, for example, an IV bag.

As understood from the above description, in syringe drive device 100 of the first embodiment, when piston 10 is pushed or pulled into/out of cylinder 6, the power is transmitted from piston-operating rod 16 and piston restraint 17 to flange 15 of piston 10. This power is stably supplied by racks 20 and 21 from the left and right sides of the central axis of piston 10.

The power compensates the momentum imparted on a piston driver, which is composed of piston-operating rod 16 and piston restraint 17 of piston 10. The piston driver therefore does not have to be resistant to the large momentum, thereby having higher driving accuracy and a smaller size. As a result, syringe drive device 100 itself can be compact.

More specifically, left and right racks 20 and 21 can be made of aluminum and have a small diameter, and pinions 28 to 32 can be made of synthetic resin. This reduces the size and weight of the piston driver, and also of the entire syringe drive device 100.

Syringe drive device 100 of the present embodiment can be portable and operated in one hand as described above.

This allows the user to mix medicines in proper places such as patients' rooms, thereby achieving efficiency improvement in mixing or preparing medicines.

Syringe drive device 100 of the first embodiment also ensures safety for the user while using it in one hand.

As shown in FIG. 1, syringe drive device 100 includes outwardly-projecting covers 38 (38a, 38b) on both sides of cylinder holder 7 over grip 2. Covers 38 accommodate teeth 27a and 27b of racks 20 and 21 exposed in notches 26, and pinions 28 to 31. This prevents the user's hand, which is holding grip 2, from coming into contact with these movable components, thereby improving safety.

As shown in FIG. 1, covers 38a and 38b at both sides of cylinder holder 7 project outwardly. When the user is holding grip 2 in the hand, the thumb and index finger are prevented from coming into contact with teeth 27a and 27b of racks 20 and 21 exposed at the bottoms over covers 38a and 38b as shown in FIG. 2. This further improves safety.

Cover 39 accommodates motor 37 and worm gear 36 as shown in FIG. 1 to improve safety. Covers 38a, 38b, and 39 are formed integrally with body case 1 to prevent an increase in the number of components, thereby contributing to a reduction in the size and weight of syringe drive device 100.

The basic structure and operation of syringe drive device 100 of the first embodiment have been described so far. The following is a description of the operation for air purging from cylinder 6, which is the main characteristic of syringe drive device 100.

When the medicine is drawn from the medicine bottle into cylinder 6 together with air, the drawn air has to be purged before the next medicine is drawn into cylinder 6 or when the medicine in the medicine bottle is injected into an IV bag.

As apparent from FIGS. 1 to 4, solution supply port 8 at one end of cylinder 6 is located eccentric to the central axis. More specifically, as shown in FIGS. 1 to 4, when the medicine is drawn from the medicine bottle into cylinder 6, solution supply port 8 is in a position lower than the center.

Cylinder 6 has scale 40 on its surface. Scale 40 appears at the top of the periphery of cylinder 6 in FIG. 1 so that the user can adjust the amount of a medicine to be drawn by looking at scale 40.

If the user pushes piston 10 forward to purge air while solution supply port 8 is in a position lower than the center, then this causes the medicine to flow out before the air is purged. To avoid this, cylinder 6 is rotated 180 degrees from the state shown in FIG. 4, thereby moving solution supply port 8 to a position higher than the center as shown in dot lines in FIG. 4.

To achieve this condition, in the first embodiment, as shown in FIG. 4, cylinder holder 7 includes rollers 41 and 42 at the lower left and lower right on the outer periphery, and roller 43 on the bottom surface of hold-down bar 11. The outer periphery of cylinder 6 is rotatably held at three positions by rollers 41, 42, and 43 in cylinder holder 7. Rollers 41, 42, and 43 do not rotate unless the user intentionally rotates cylinder 6. Cylinder 6 is held on cylinder holder 7 while being pressed against rollers 41 and 42 by projections 11c of hold-down bar 11.

The user rotates cylinder 6 by 180 degrees from the state shown in FIG. 4 while holding the outer periphery of cylinder 6. As a result, solution supply port 8 is moved to a position higher than the center.

In this case, the user can rotate cylinder 6 while it is being held in cylinder holder 7 and is also being pressed by hold-down bar 11. This makes it easy for the user to prepare for air purging, such as to rotate cylinder 6, thereby improving workability.

When the user is preparing medicines by holding grip 2 in the right hand like holding a pistol, and holding a medicine bottle in the left hand, both hands are occupied. In syringe drive device 100 of the first embodiment where cylinder 6 is rotatably held in cylinder holder 7, however, the user can take the left hand off the medicine bottle and then rotate cylinder 6 by the left hand. This makes it easy for the user to prepare for air purging such as to rotate cylinder 6, thereby improving workability.

In this situation, the user can push piston 10 forward to smoothly purge the air from the upper part of cylinder 6 through solution supply port 8. When user purges air, the injection needle (not shown) is not attached to the medicine bottle in most cases, but is attached in some cases. In either case, solution supply port 8 is positioned at the top of the periphery of cylinder 6 in the first embodiment, preventing the medicine from flowing to the outside of cylinder 6 during the air purging.

When purging the air completely, the user can rotate cylinder 6 by 180 degrees to return it to the state shown by solid lines in FIG. 4, thereby moving solution supply port 8 to a position lower than the center. This makes it easier for the user to draw medicines while watching scale 40.

In this case, the user can easily rotate cylinder 6 by, for example, the left hand, while it is being held in cylinder holder 7 and is also being pressed by hold-down bar 11. This further improves workability.

When cylinder 6 is rotated, flange 14 formed on the outer periphery of opening 9 at the other end of cylinder 6 is also rotated. The groove (not shown) of cylinder holder 7 into which flange 14 is fitted is deep enough not to disturb the rotation of flange 14.

Figure 5:
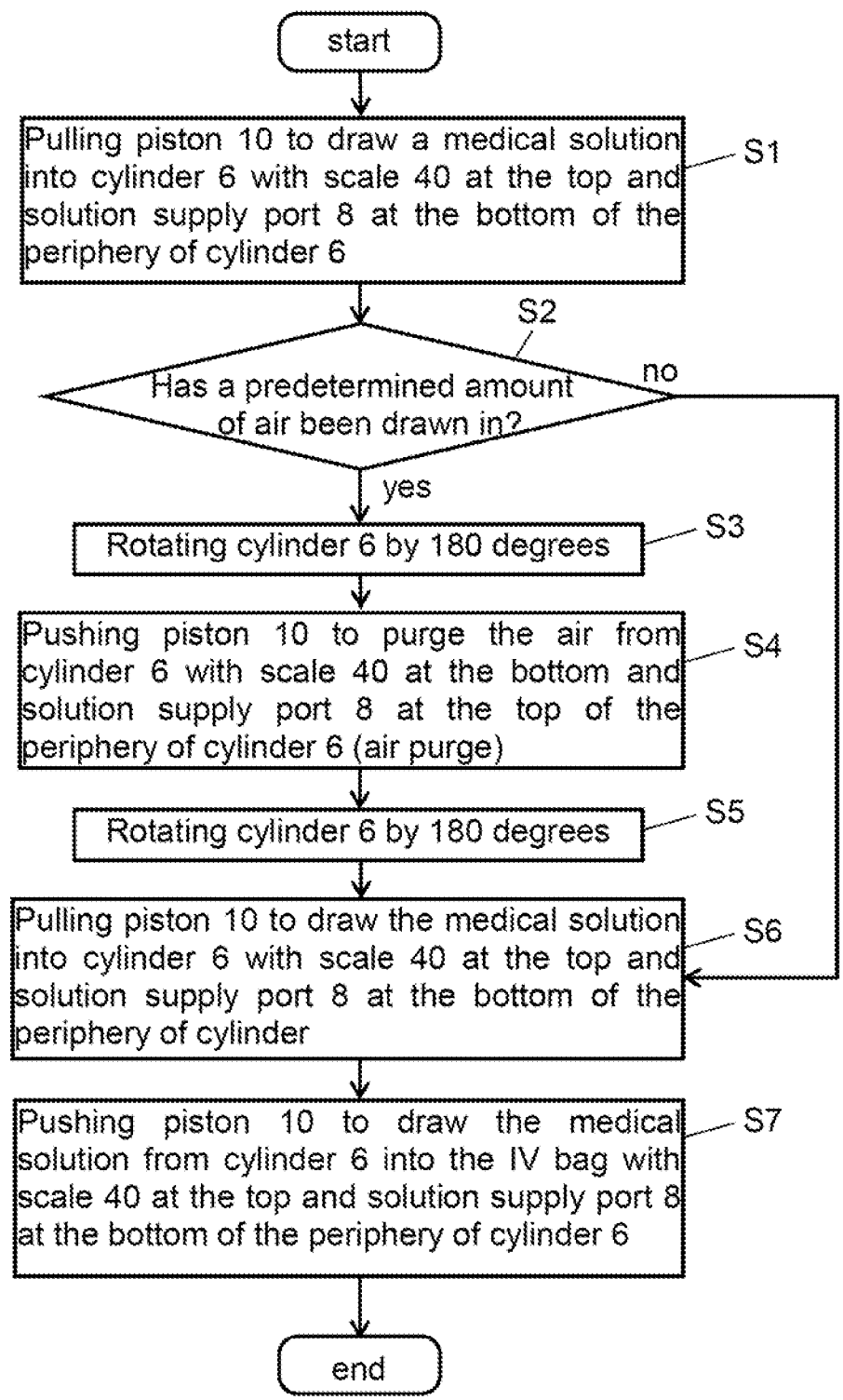
FIG. 5 is a flowchart showing how to rotate the cylinder in the first embodiment of the invention.

The following is a description of how to rotate cylinder 6 in syringe drive device 100 of the first embodiment. FIG. 5 is a flowchart showing how to rotate cylinder 6 in syringe drive device 100 of the first embodiment.

In FIG. 5, the user pulls out piston 10 to draw a medical solution from the medicine bottle into cylinder 6 with scale 40 at the top and solution supply port 8 at the bottom of the periphery of cylinder 6 (Step S1).

The user determines whether, when the medical solution has been drawn into cylinder 6 at Step S1, a predetermined amount of air has also been drawn in (Step S2).

When it is determined at Step S2 that the predetermined amount of air has been drawn, the user rotates cylinder 6 by 180 degrees by the hand (the left hand in the first embodiment) opposite to the hand holding grip 2 of syringe drive device 100 (Step S3).

After the rotation of cylinder 6 at Step S3, scale 40 is positioned at the bottom of the periphery of cylinder 6, and solution supply port 8 at the top. In this situation, the user again holds the medicine bottle, and pulls the tip of the injection needle out of the liquid into the air in the medicine bottle. Next, the user pulls out piston 10 to completely draw the medical solution remaining in the injection needle into cylinder 6. Then, the user pushes piston 10 to purge the air from cylinder 6 with solution supply port 8 at the top and the medical solution at the bottom of the periphery of cylinder 6. This allows the user to purge the air from the top of cylinder 6 through solution supply port 8 (Step S4).

After a necessary amount of air is purged at Step S4, the user rotates cylinder 6 by 180 degrees by the hand (the left hand in the first embodiment) opposite to the hand holding grip 2 of syringe drive device 100 (Step S5).

Then, the user pulls piston 10 to draw the medical solution into cylinder 6 with scale 40 at the top and solution supply port 8 at the bottom of the periphery of cylinder 6. If it is determined that the predetermined amount of air has not been drawn in at Step S2, the process proceeds to Step S6 by skipping Steps S3 to S5. The medical solution to be drawn in at this step may be the same or different from the medical solution drawn in at Step S1 (Step S6).

After the process from Steps S1 to S6 is repeated a necessary number of times, the user pushes piston 10 to inject the medical solution from cylinder 6 into the IV bag with scale 40 at the top and solution supply port 8 at the bottom, and to mix it with other medical solutions (Step S7).

Through the above-described process, syringe drive device 100 drives cylinder 6 including its rotation.

When cylinder 6 is rotated, piston 10 may be rotated in unison therewith. This prevents an excessive load from being applied to the tip of piston 10, which is hermetically sealed with an O-ring or a gasket. In addition, the medical solutions in cylinder 6 are prevented from being mixed against the user's intention.

Second Embodiment

Figure 6:
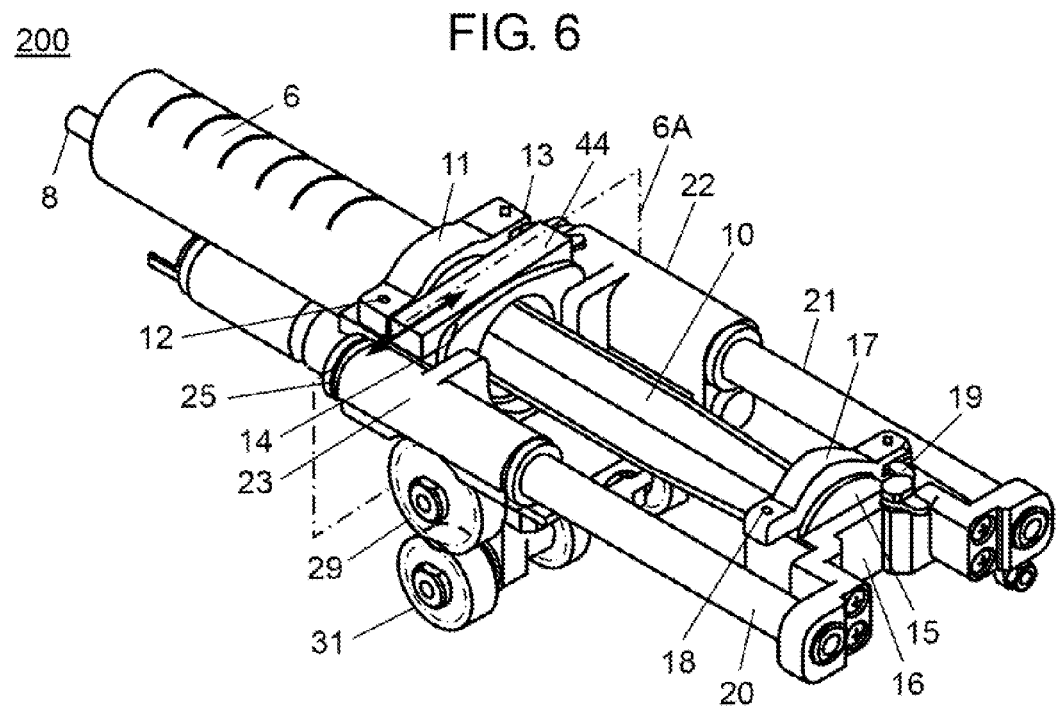
FIG. 6 is a perspective view of mechanism elements of a syringe drive device according to a second embodiment of the invention.
Figure 7:
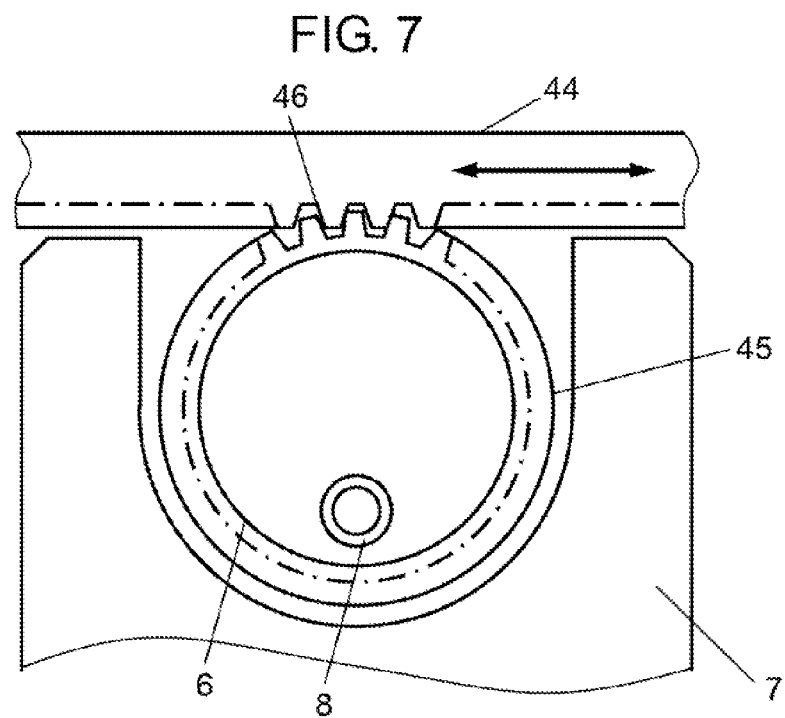
FIG. 7 is a front view of an essential part of the syringe drive device according to the second embodiment of the invention.

In syringe drive device 100 of the first embodiment, the user rotates cylinder 6 by touching its outer periphery. Syringe drive device 200 of a second embodiment of the invention includes operating rod 44 with which the user rotates cylinder 6 as shown in FIGS. 6 and 7. FIG. 6 is a perspective view of mechanism elements of syringe drive device 200, and FIG. 7 is a front view of an essential part of syringe drive device 200. In FIG. 7, hold-down bar 11 is not illustrated so as to clearly show the layout on plane 6A of the outer periphery of cylinder 6, that is, operating rod 44, pinion 45, and a part of cylinder holder 7.

The following is a detailed description of syringe drive device 200. Pinion 45 is previously fixed adjacent to flange 14 on the outer periphery of cylinder 6. Next, operating rod 44 is slidably attached to syringe drive device 200. When the user operates operating rod 44, teeth 46 of operating rod 44 is engaged with pinion 45, thereby rotating cylinder 6. In other words, operating rod 44 is slidably provided over cylinder holder 7. Although not shown in FIG. 7 in detail, pinion 45 fixed on the outer periphery of cylinder 6 has teeth throughout its periphery, that is, 360 degrees, or at least 180 degrees if the rotation direction can be flipped.

Assume that the user is preparing medicines by holding grip 2 in the right hand like holding a pistol, and a medicine bottle in the left hand. Although both hands are occupied, since cylinder 6 is rotatably held in cylinder holder 7, the user can take the left hand off the medicine bottle while solution supply port 8 is positioned at the top, and then operate operating rod 44 by the left hand. Thus, syringe drive device 200 is extremely user-friendly, allowing the user to rotate cylinder 6 easily.

Figure 8:
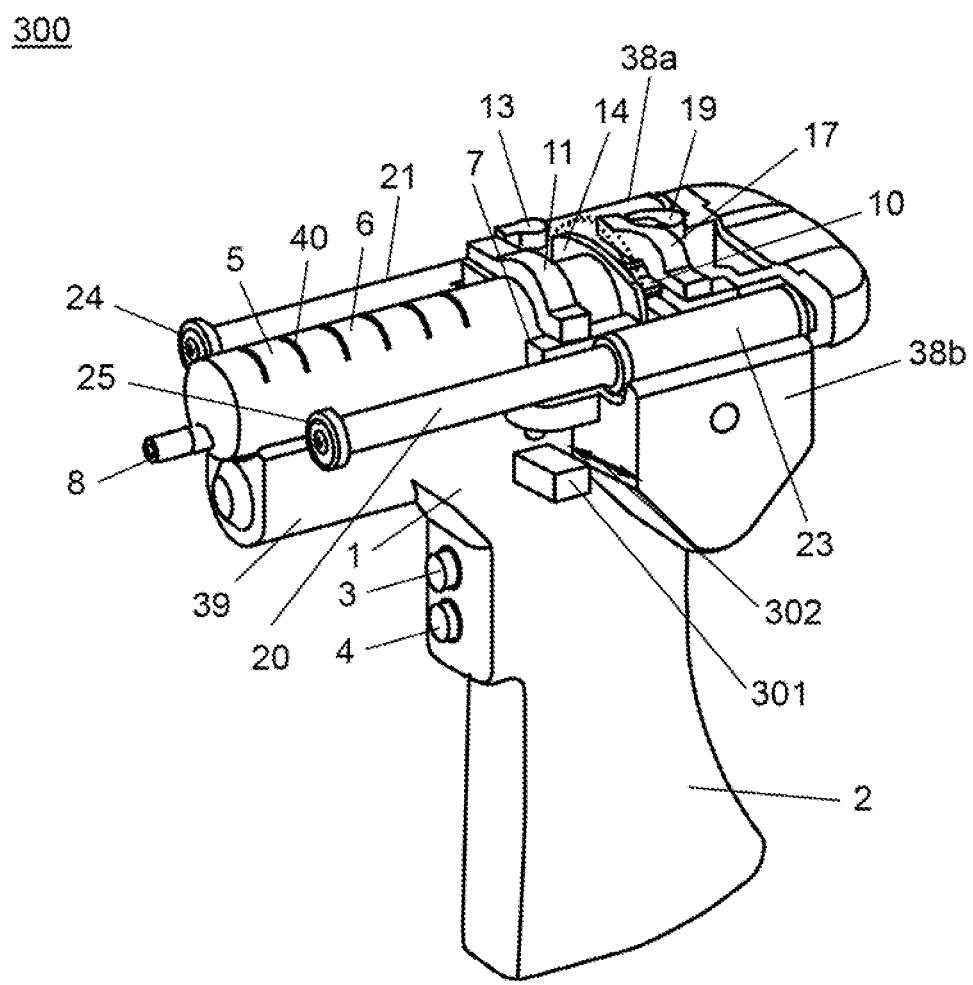
FIG. 8 is a perspective view of another syringe drive device according to the second embodiment of the invention.
Figure 9:
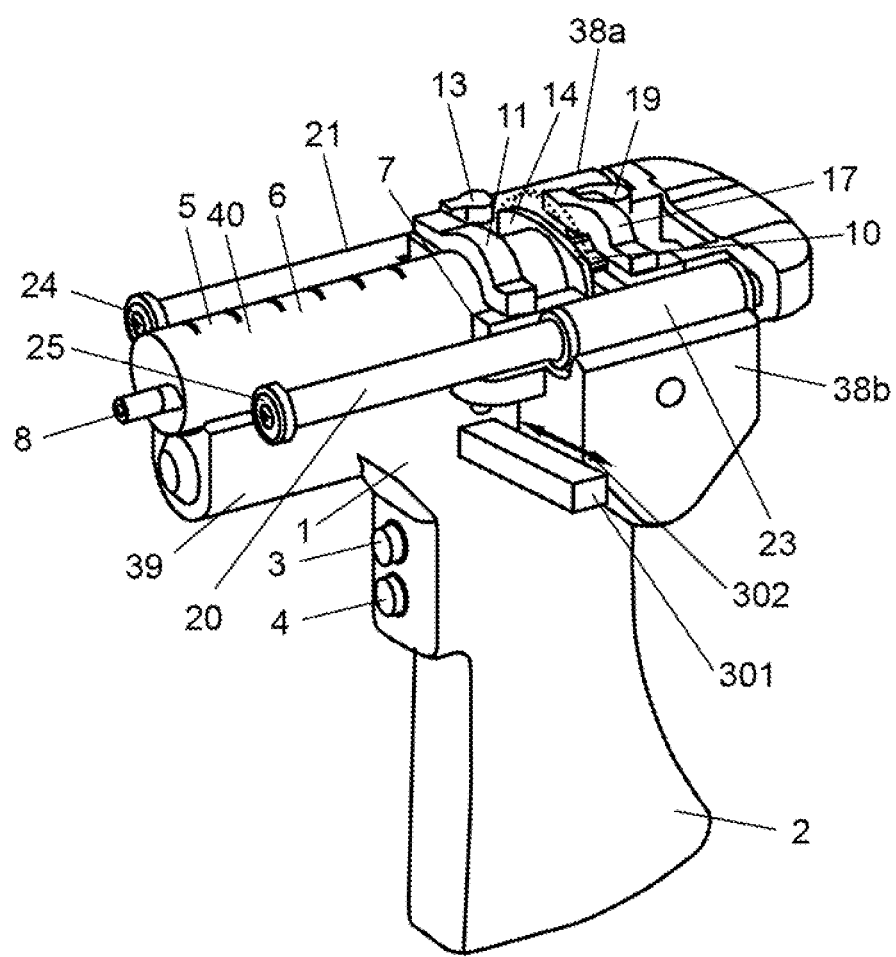
FIG. 9 is a perspective view of the other syringe drive device according to the second embodiment of the invention.

FIGS. 8 and 9 are perspective views of syringe drive device 300, which is another example according to the second embodiment. Unlike syringe drive device 200, syringe drive device 300 includes operating rod 301 for rotating cylinder 6 under cylinder 6. In the same manner as in syringe drive device 200 shown in FIGS. 6 and 7, the user can move operating rod 301 in the direction of arrow 302 shown in FIGS. 8 and 9 to engage the teeth (not shown) of operating rod 301 with pinions (not shown) formed on the outer periphery of cylinder 6. The user rotates cylinder 6 to move solution supply port 8 to the top position in order to purge the air from cylinder 6, and to the bottom position in order to watch scale 40.

As shown in FIGS. 8 and 9, in syringe drive device 300, operating rod 301 is provided under the cylinder (on the grip). This allows the user to operate operating rod 301 with the right thumb while holding grip 2 in the right hand. Thus, the user can purge air from cylinder 6 with grip 2 in the right hand.

Figure 10A:
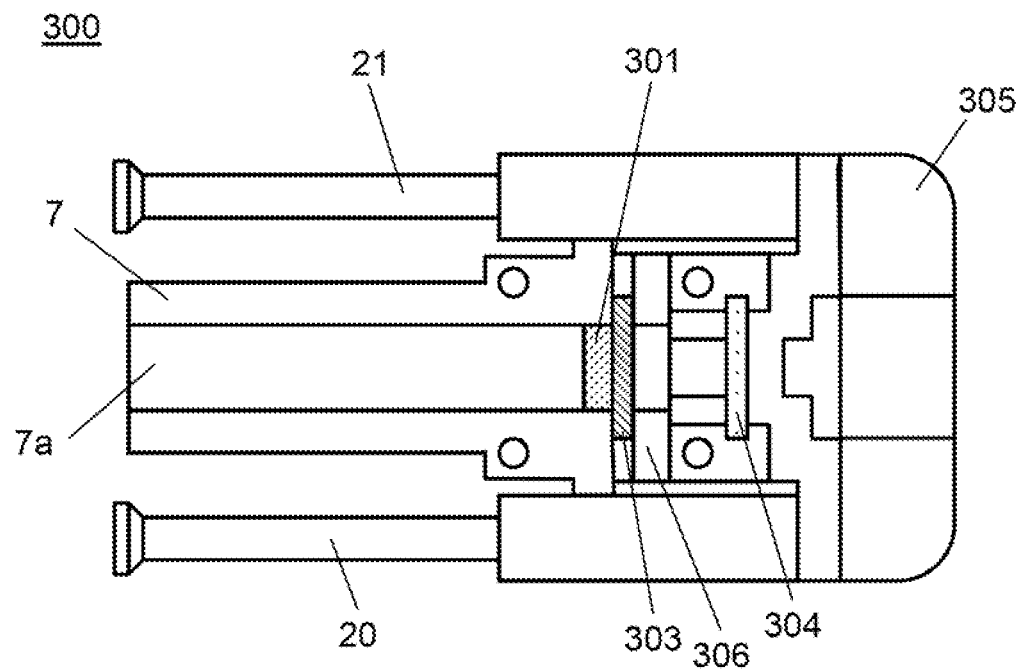
FIG. 10A is a schematic plan view of the other syringe drive device according to the second embodiment of the invention.
Figure 10B:
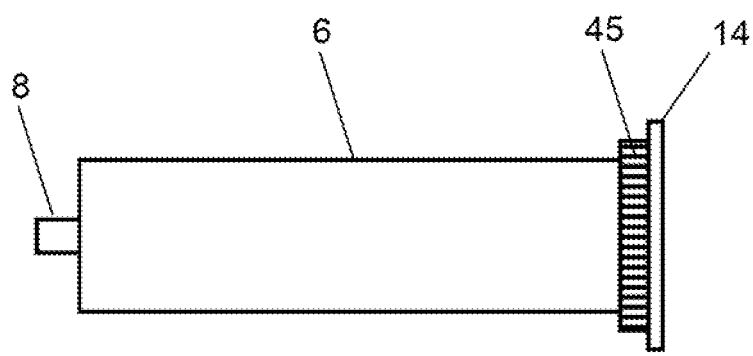
FIG. 10B is a schematic plan view of a syringe placed in the other syringe drive device.
Figure 11A:
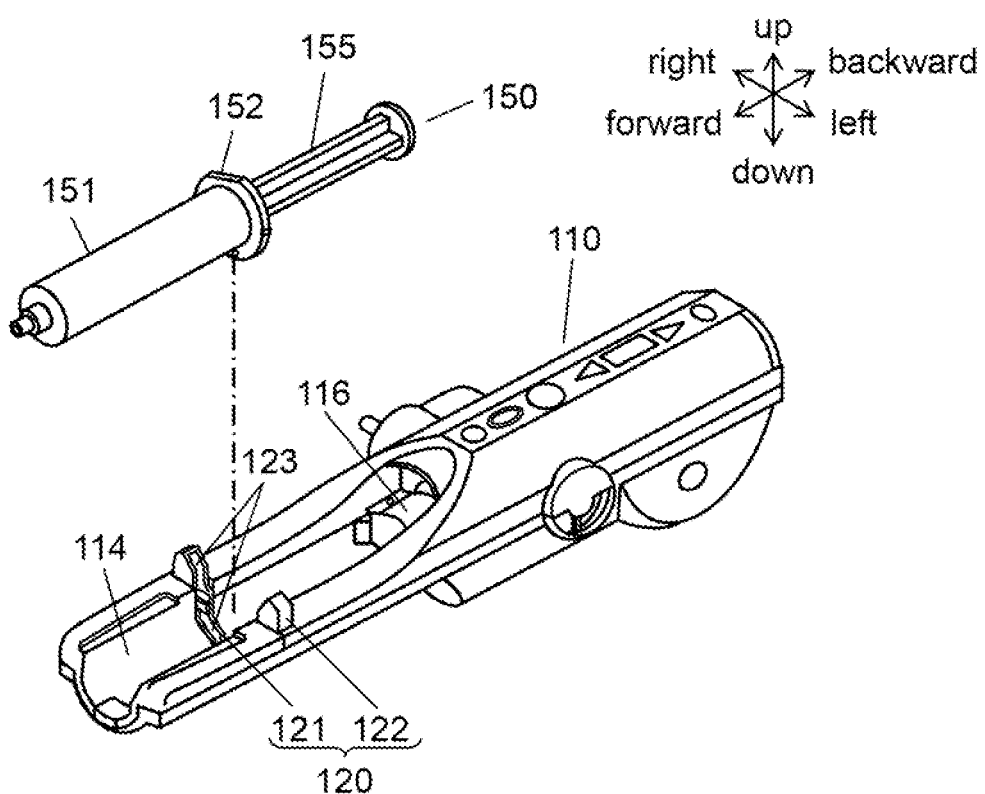
FIG. 11A is a perspective view of a conventional syringe drive device.
Figure 11B:
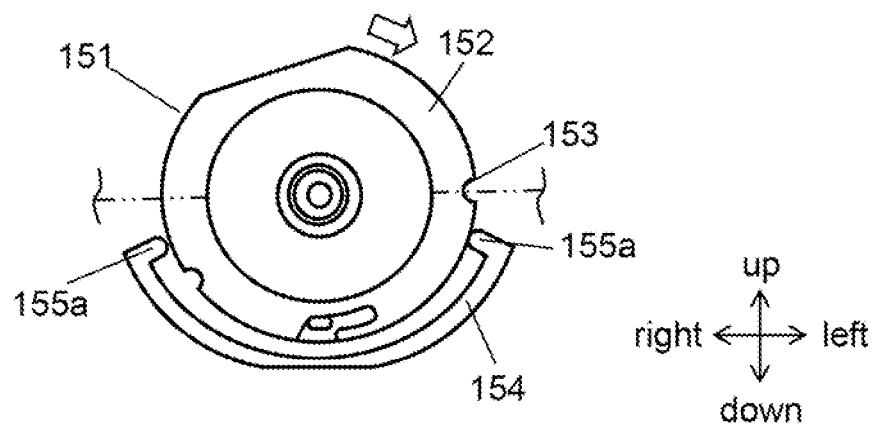
FIG. 11B is an enlarged view of an essential part of the conventional syringe drive device.

FIG. 10A is a schematic plan view of syringe drive device 300, and FIG. 10B is a schematic plan view of syringe 5 placed in syringe drive device 300.

The syringe shown in FIG. 10B is placed in syringe drive device 300 as shown in FIG. 10A. Syringe drive device 300 includes cylinder holder 7 having recess 7a, and grooves 303, 304. Cylinder 6 of the syringe is placed in recess 7a. Part of pinion 45 is placed adjacent to the upper part of operating rod 301. Part of flange 14 is fitted into groove 303. Part of a flange (not shown) at the rear end of the piston (not shown) to be inserted into cylinder 6 is fitted into groove 304. When the user pulls the piston using piston driver 305, flange 14 of cylinder 6 is pulled rearward. For this reason, cylinder holder 7 includes stopper 306 at its rear end.

With this structure, the syringe can surely be fitted into grooves 303 and 304 in syringe drive device 300, and can be surely and safely driven by piston driver 305 such that medical solution can be forced in or out. In addition, operating rod 301 facilitates the user to see scale 40 of cylinder 6 and to purge air from cylinder 6.

Third Embodiment

In a third embodiment of the invention, flange 14 formed at opening 9 of cylinder 6 has a circular shape, and is provided with pinion 45 around it.

In this case, cylinder holder 7 includes an operating rod (not shown) for rotating cylinder 6 in place of operating rod 44 shown in FIG. 7. The operating rod is engaged with pinion 45 of flange 14 formed at opening 9 of cylinder 6.

Cylinder holder 7 may have a locking part (not shown) for preventing rotation of the cylinder in the first and second embodiments shown in FIGS. 1 to 5 and FIGS. 6 to 10B, respectively, and also in the third embodiment having flange 14 with pinion 45. The locking part allows the user to rotate the cylinder as needed. The locking part has an operation button disposed at a position that the user can operate while holding grip 2 in the right hand, for example, under operation button 4. As a result, the syringe drive device becomes more user-friendly including the locking part for preventing rotation of the cylinder.

As described hereinbefore, the syringe drive device of the invention is extremely user-friendly, allowing the user to purge air from the cylinder easily by rotating the cylinder, and also to perform this operation repeatedly.

Thus, the syringe drive device, which reduces nurses' work burden including the mixing of injection medicines, is expected to be suitable for hospital use.

The invention claimed is:

1. A syringe drive device to hold and drive a syringe, the syringe including a cylinder and a piston inserted in the cylinder, the cylinder having a solution supply port at an eccentric position, the syringe drive device comprising:
   a cylinder holder to hold the cylinder such that the cylinder can rotate around an axis of the cylinder;
   a rotation aid to rotate the cylinder held in the cylinder holder by a predetermined angle around the axis of the cylinder; and
   a piston driver to drive the piston in an axial direction thereof with respect to the cylinder held in the cylinder holder;
   wherein the cylinder holder includes a hold-down bar in an upper part thereof;
   wherein at least one roller is located in a recess formed in the cylinder holder; and
   wherein the at least one roller is located on a bottom surface of the hold-down bar facing the cylinder holder.

2. The syringe drive device of claim 1, wherein the rotation aid vertically flips the eccentric position of the solution supply port of the cylinder by rotating the cylinder held in the cylinder holder by 180 degrees around the axis.

3. A syringe drive device to hold and drive a syringe, the syringe including a cylinder and a piston inserted in the cylinder, the cylinder having a solution supply port at an eccentric position, the syringe drive device comprising:
   a cylinder holder to hold the cylinder such that the cylinder can rotate around an axis of the cylinder;
   a rotation aid to rotate the cylinder held in the cylinder holder by a predetermined angle around the axis of the cylinder; and
   a piston driver to drive the piston in an axial direction thereof with respect to the cylinder held in the cylinder holder;
   wherein the cylinder is held in the cylinder holder with a gear provided near a flange of the cylinder.

4. The syringe drive device of claim 3, further comprising:
   an operating rod near the cylinder holder, the operating rod rotating the cylinder to be engaged with the gear provided in the cylinder.

5. A syringe drive device to hold and drive a syringe, the syringe including a cylinder and a piston inserted in the cylinder, the cylinder having a solution supply port at an eccentric position, the syringe drive device comprising:
   a cylinder holder to hold the cylinder such that the cylinder can rotate around an axis of the cylinder;
   a rotation aid to rotate the cylinder held in the cylinder holder by a predetermined angle around the axis of the cylinder; and
   a piston driver to drive the piston in an axial direction thereof with respect to the cylinder held in the cylinder holder;
   wherein the cylinder includes a gear provided on an outer periphery of a flange; and
   wherein an operating rod is provided to rotate the cylinder to be engaged with the gear provided on the outer periphery of the flange of the cylinder.

6. The syringe drive device of claim 4, wherein the hold-down bar and the operating rod are slidably provided in an upper part of the cylinder holder.

7. A syringe drive device to hold and drive a syringe, the syringe including a cylinder and a piston inserted in the cylinder, the cylinder having a solution supply port at an eccentric position, the syringe drive device comprising:
   a cylinder holder to hold the cylinder such that the cylinder can rotate around an axis of the cylinder;
   a rotation aid to rotate the cylinder held in the cylinder holder by a predetermined angle around the axis of the cylinder; and
   a piston driver to drive the piston in an axial direction thereof with respect to the cylinder held in the cylinder holder;
   wherein an operation button of a locking part to prevent rotation of the cylinder is disposed under the piston driver.

8. A syringe drive device to hold and drive a syringe, the syringe including a cylinder and a piston inserted in the cylinder, the cylinder having a solution supply port at an eccentric position, the syringe drive device comprising:
   a cylinder holder to hold the cylinder such that the cylinder can rotate around an axis of the cylinder;
   a rotation aid to rotate the cylinder held in the cylinder holder by a predetermined angle around the axis of the cylinder; and
   a piston driver to drive the piston in an axial direction thereof with respect to the cylinder held in the cylinder holder;

wherein the cylinder holder includes a locking part to prevent rotation of the cylinder.

* * * * *